(12) United States Patent
Haras et al.

(10) Patent No.: US 7,623,905 B2
(45) Date of Patent: Nov. 24, 2009

(54) METHOD FOR PRODUCTION OF COMPUTER-TOMOGRAPHIC SCANS DURING AN INTERVENTION

(75) Inventors: Gabriel Haras, Mücke (DE); Rainer Raupach, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 132 days.

(21) Appl. No.: 11/491,104

(22) Filed: Jul. 24, 2006

(65) Prior Publication Data
US 2007/0019780 A1 Jan. 25, 2007

(30) Foreign Application Priority Data
Jul. 25, 2005 (DE) .................. 10 2005 034 683

(51) Int. Cl.
*A61B 5/05* (2006.01)
(52) U.S. Cl. .................. 600/425; 600/427; 378/4; 378/11; 378/15; 378/17; 378/20; 378/21; 378/23; 378/25; 378/26; 378/27
(58) Field of Classification Search .......... 600/425, 600/427; 378/4, 11, 15, 17, 20, 21, 23, 25–27
See application file for complete search history.

(56) References Cited

U.S. PATENT DOCUMENTS

| | | | | |
|---|---|---|---|---|
| 5,023,895 A | * | 6/1991 | McCroskey et al. ............ 378/4 |
| 5,740,222 A | | 4/1998 | Fujita et al. | |
| 6,167,296 A | * | 12/2000 | Shahidi ...................... 600/427 |
| 6,233,303 B1 | * | 5/2001 | Tam .............................. 378/4 |
| 6,341,152 B1 | | 1/2002 | Sugihara | |
| 6,817,762 B2 | * | 11/2004 | Proksa ........................ 378/206 |
| 2002/0114423 A1 | | 8/2002 | Grass et al. | |
| 2003/0099323 A1 | * | 5/2003 | Nagata et al. .................. 378/4 |
| 2006/0149147 A1 | * | 7/2006 | Yanof ......................... 600/424 |

OTHER PUBLICATIONS

Examination Report for corresponding app. 2005PO6326, Jun. 2, 2006.

* cited by examiner

*Primary Examiner*—Brian Casler
*Assistant Examiner*—James Kish
(74) *Attorney, Agent, or Firm*—Harness, Dickey & Pierce, P.L.C.

(57) ABSTRACT

A method is disclosed for production of computer-tomographic scans via a CT system of a patient during an intervention with an instrument. An X-ray tube is moved on a rotation plane around the patient in order to produce a beam cone, and a detector with a plurality of detector elements measuring the radiation intensity after passing through the patient. Computer-tomographic scans are reconstructed from the measured values in a computation unit. The central direction of the beams of the scanning beam cone is set at an angle to the intervention axis, and at least one slice plane which differs from the rotation plane of the beam cone is displayed on a display.

20 Claims, 4 Drawing Sheets

METHOD FOR PRODUCTION OF COMPUTER-TOMOGRAPHIC SCANS DURING AN INTERVENTION

PRIORITY STATEMENT

The present application hereby claims priority under 35 U.S.C. §119 on German patent application number DE 10 2005 034 filed Jul. 25, 2005, the entire contents of which is hereby incorporated herein by reference.

FIELD

The invention generally relates to a method for production of computer-tomographic scans. For example, it may relate to one for production via a CT system of a patient during an intervention with an instrument, with at least one X-ray tube being moved on a rotation plane around the patient in order to produce a beam cone, and a detector with a large number of detector elements measuring the radiation intensity after passing through the patient, the position and the orientation of the patient relative to a gantry which holds the X-ray tube and the detector being controlled by a control unit, and computer-tomographic scans being reconstructed from the measured values in a computation unit with the aid of computer programs.

BACKGROUND

Methods for the production of computer-tomographic scans by way of a CT system during an intervention on a patient with an instrument are generally known.

An intervention with the aid of a medical instrument with CT observation in this case relates to a metallic needle which is used, for example, to carry out a nerve blockade or to treat a tumor, with this needle being inserted into the body in a known manner parallel to the scanning X-ray beams, or the gantry being pivoted with its rotation plane on which the X-ray tube and the opposite detector are located to such an extent that the X-ray beams run parallel to the instrument, and reconstructed images are then made available to the operator, with these images being arranged in the immediate vicinity of and parallel to the instrument. An image is generally displayed which shows a longitudinal section through the intervention instrument in order to provide the operator with as good an overview as possible of the area directly surrounding the intervention instrument. The intervention direction is in this case generally oriented at right angles to the system axis or longitudinal axis of the patient.

It has been found that artifacts which lead to an unsatisfactory image display are produced during computer-tomographic scans such as these.

SUMMARY

A method, in at least one embodiment, is provided which reduces or even avoids these artifacts occurring there.

The inventors have discovered that the reason for the artifacts that occur is, on the one hand, the scattered radiation, which is made stronger in particular by the metallic material of the instrument and the long path of the radiation through the instrument in the case of irradiation on the longitudinal axis of the instrument. On the other hand, the major reduction in the radiation intensity also results in a poor signal-to-noise ratio in the radiation shadow of the instrument. Furthermore, the passage of the radiation through the instrument over a relatively long distance also results in major hardening of the radiation, that is to say in a significantly different change in the radiation spectrum in the radiation shadow of the instrument, which leads to a change in the absorption behavior in the tissue.

The inventors have also discovered that it is possible to bypass this scattered radiation at least in the area of interest, that is to say in the intervention direction and between an intervention needle and a target region in the patient, by scanning this area of interest with beams which do not pass through the intervention instrument, thus scanning a region. On the one hand, this results in less scattered radiation being produced, while on the other hand there is scarcely any change in the radiation spectrum in the area of interest, and the signal-to-noise ratio remains in the good range. A scan such as this is possible, for example, by inclining the gantry with its rotation plane with respect to the z axis, so that the instrument is undercut by the X-rays, thus allowing considerably better imaging. Nevertheless, by appropriate reformatting of the available image data, it is also possible for the operator to use a different slice for the CT display, preferably an axial slice, through the intervention instrument to the target region.

In addition to the direct inclination of the rotation plane of the beam cone or of the gantry, it is, however, also possible to produce an asymmetric shift of the shutter with an appropriately broad detector so that only the X-ray beams which run obliquely at the side are used for reconstruction. The other beams, which are not required, are masked out in order to reduce the dosage, so that this type of arrangement likewise allows oblique irradiation of the intervention region, thus also making it possible to considerably reduce the artifacts which were previously present and result from the radiation passing through the instrument.

On the basis of this idea of at least one embodiment of the invention as described above, the inventors propose that methods which are known per se for production of computer-tomographic scans via a CT system of a patient during an intervention with an instrument, preferably at right angles to a system axis of the CT system along an intervention axis, with at least one X-ray tube being moved on a rotation plane around the patient in order to produce a beam cone, and a detector with a large number of detector elements measuring the radiation intensity after passing through the patient, the position and the orientation of the patient relative to a gantry which holds the X-ray tube and the detector being controlled by a control unit, and computer-tomographic scans being reconstructed from the measured values in a computation unit with the aid of computer programs, be improved such that the central direction of the beams of the scanning beam cone is set at an angle to the intervention axis, and at least one slice plane which differs from the rotation plane of the beam cone is displayed on a display. In this case, an axial image display, that is to say a slice plane at right angles to the system axis, can preferably be chosen.

The intervention axis can be detected and, for example in the case of a needle as the intervention instrument, corresponds to the longitudinal axis of the needle or else the connecting line between a target region and the intervention instrument, or the incision point of the intervention instrument.

The inclination of the central direction of the scanning beam cone may be produced, by example, by inclination of the rotation plane of the gantry with respect to the system axis of the CT. However, it is also possible to produce the inclination of the central direction of the scanning beam cone by asymmetric setting of shutters in the beam path.

An instrument longitudinal axis may be used as the intervention axis, and may be detected by evaluation of CT scans. By way of example, a pattern recognition method can be used for this process, which detects the instrument in the CT scans and determines its instantaneous orientation and position.

However, there are also other possible ways, which are known per se, for determination of the longitudinal axis of the instrument. For example, transmitters and receivers which are fitted to the instrument and to the CT system can determine the position and orientation of the instrument, or else it is possible to fit optical sensors and markings to the instrument and to detect the instrument position and orientation relative to the CT system by appropriate image evaluation processes.

A further possible way to determine the intervention axis is to predetermine a target region for the intervention and to regard the connection from one part of the instrument, preferably its end, to the target region as the intervention axis. At the start of the intervention, this corresponds to the line between the incision point and the actual target region.

According to at least one embodiment of the invention, the maximum angle which can be set between the gantry and the intervention axis which can be used to display a predetermined region on the plane of the intervention axis can also be calculated automatically during the scan, and this angle is adjusted such that it is continuously matched. Thus, in the case of this method, a relatively steep angle with respect to the system axis of the CT system can be set at the start of the intervention, when the intervention instrument is still a relatively long way away from the target region, while the inclination of the beam cone can be increased as the instrument approaches the target region, since the region which is of interest in the end has a smaller extent so that relatively oblique irradiation is thus possible for a sufficiently large display of the region, and the display plane can nevertheless still correspond to the instrument axis.

By way of example, the area between the target region of the intervention and the instrument can be used as the predetermined region to be displayed. However, it is also possible to use a predetermined part of the instrument and a predetermined distance in the intervention direction as the predetermined region to be displayed. It should be noted that, in at least one embodiment, it is also within the scope of the invention to also adjust the positioning of the patient in the direction of the system axis of the CT system in addition to the inclination setting of the beam cone, in order to keep the region being viewed optimally in the beam path of the X-ray tube.

In at least one embodiment, it is also within the scope of the invention to carry out a 2D reconstruction on the beam plane as a reconstruction method, but for the slices to be displayed by reformatting on the plane of the intervention axis. In practice, this display will generally coincide with the axial display, but in at least one embodiment, it should expressly be noted that other slice planes or intervention axes are also within the scope of this invention.

On the other hand, it is also possible to carry out a 3D reconstruction of a large number of individual voxels, in which case it may be advantageous to reconstruct only the voxels of a predetermined area or an area to be displayed, in order to avoid loading the reconstruction speed with the reconstruction of regions which will no longer be required later.

Plane elements which are located in the immediate vicinity of the instrument, possibly a part of the instrument, and whose orientation is parallel to the intervention direction can be selected as the predetermined area of the voxels to be reconstructed.

It is also possible to select plane elements which are located between the target region and the instrument and whose orientation is likewise parallel to the intervention direction as the predetermined area of the voxels to be reconstructed.

Furthermore, in the case of a 3D reconstruction, both a plane along the intervention axis and an axial display can be shown on a display.

In at least one embodiment, on the basis of the method described above, the inventors also propose a computer-tomographic system which has at least one X-ray tube for production of a beam cone which is moved on a rotation plane around the patient, and a detector having a large number of detector elements, which measures the radiation intensity after passing through the patient. Furthermore, this CT system has a control unit for controlling the relative position and orientation of the patient with respect to a gantry which holds the X-ray tube and the detector, and a computation unit for evaluation of the measured values of the detector and for reconstruction of computer-tomographic scans with the aid of computer programs, in which case, according to the invention, the CT system also has computer programs which, when they are run on the computation and control unit, carry out the method steps of the method outlined above.

BRIEF DESCRIPTION OF THE DRAWINGS

The invention will be described in more detail in the following text with reference to the example embodiments and with the aid of the figures, which illustrate only these features which are required for understanding of the invention and in which the following reference signs are used: 1: CT system; 2: X-ray tube; 2.1: focus; 3: detector; 3.x: detector elements; 4: system axis; 5: CT housing; 6: moveable patient couch; 7: patient; 8: opening between the X-ray tube and the detector; 9: control and computation unit; 9.1: display; 10: data/control line; 11: instrument; 12: beam cone; 12.M: center beam of the scanning beam cone; 13: target region for the intervention; 14: beam shutter; 15: rotation plane of the gantry; 16: scattered radiation; 17: connecting line between the instrument and target region; 18: reconstruction plane; 19: display plane parallel to the intervention axis; 20: intervention axis; 21: instrument longitudinal axis; $Prg_1$-$Prg_n$: computer programs; R: rotation axis of the gantry; $\alpha$: inclination angle of the rotation axis with respect to the system axis.

In detail.

DETAILED DESCRIPTION OF THE EXAMPLE EMBODIMENTS

Figure 1:
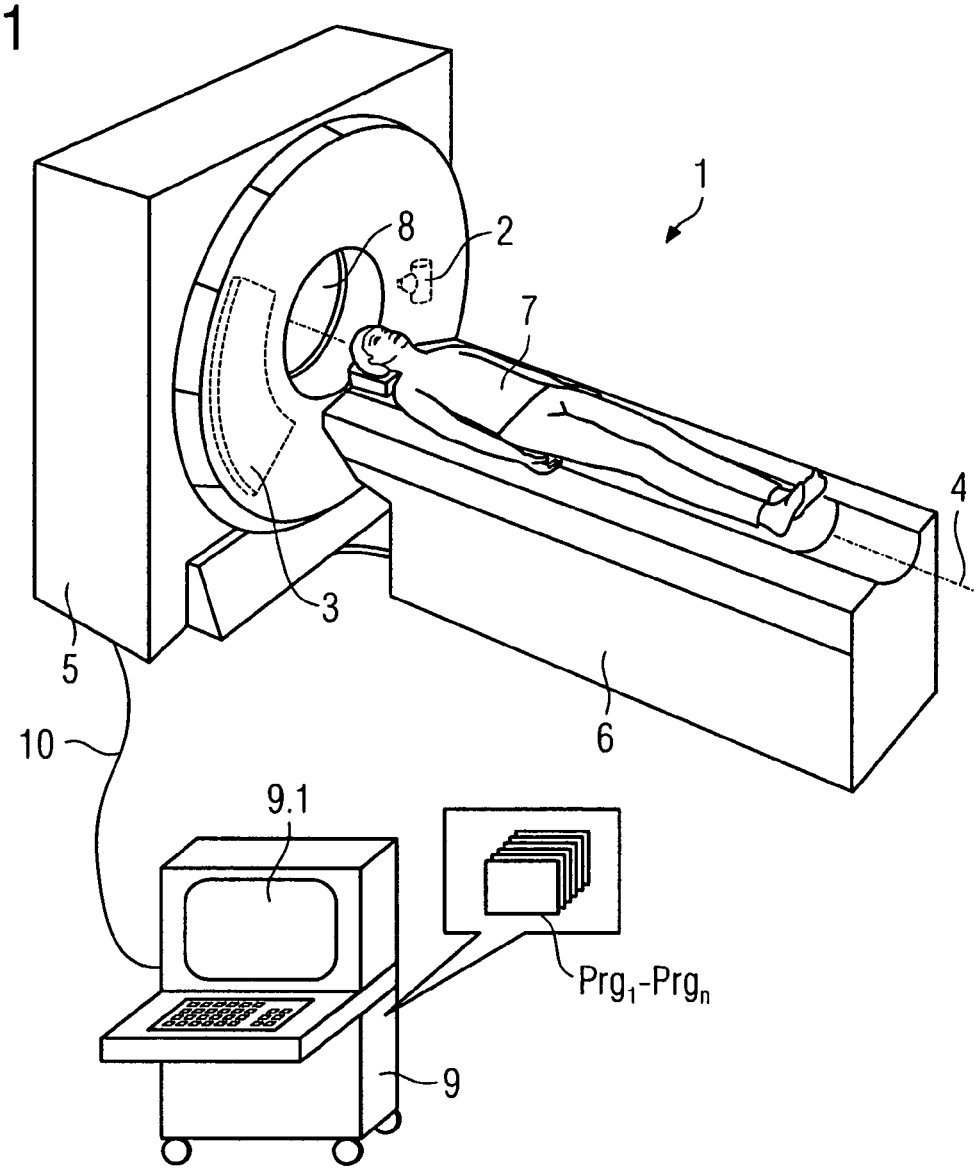
FIG. 1 shows an example of a CT system for carrying out the method according to an embodiment of the invention.

FIG. 1 shows a CT system 1 according to an embodiment of the invention with a CT housing 5 in which a gantry is located, which is not illustrated in any more detail but on which an X-ray tube 2 and a detector 3, opposite, are arranged. A patient 7 is located on a patient couch 6 which can be moved in the system axis direction 4, and can be moved into the beam path through an opening 8 in the gantry, for the scan. The control, data gathering and data evaluation with reconstruction are carried out by the computation and control unit 9, which is connected via the data and control line 10 to the gantry and to the moveable patient couch, with the computation and control unit having stored programs $Prg_1$ to $Prg_n$ which are run during operation and carry out the method according to an embodiment of the invention. The reconstructed and reformatted displays based on the method according to an embodiment of the invention can be shown on a display 9.1 on the computation and control unit 9, or on other separate screens.

Figure 2:
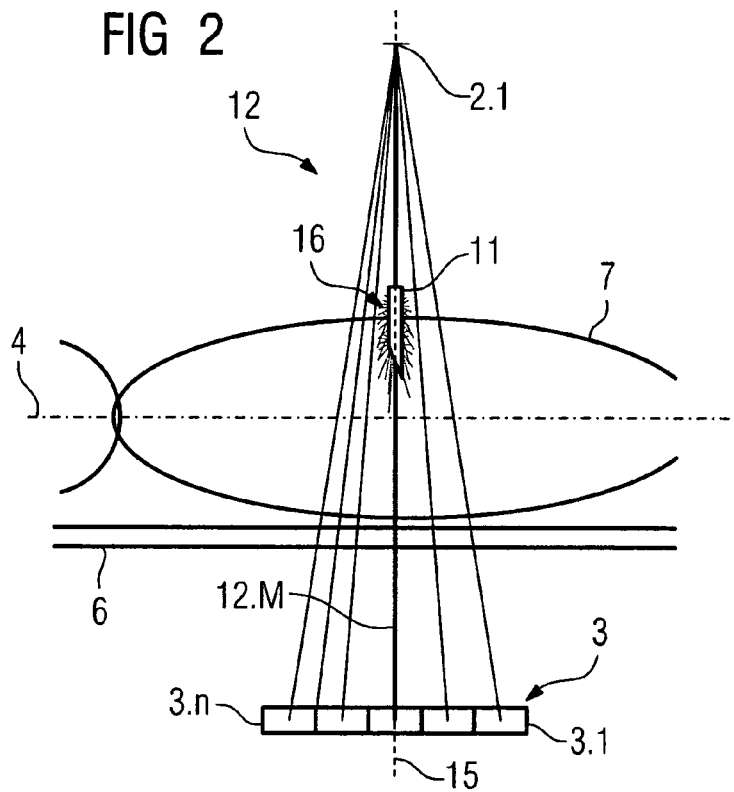
FIG. 2 shows a schematic illustration of a longitudinal section through a CT with a patient and an intervention instrument according to the prior art.

FIG. 2 shows the current prior art, schematically illustrating a longitudinal section through a patient 7 who is lying on a patient couch 6. A beam cone 12 which originates from a focus 2.1 passes through the patient 7 to an opposite detector 3 with detector elements 3.1 to 3.$n$. In order to carry out the scan for the computer-tomographic evaluation, the focus 2.1 and the detector 3 are moved around a rotation axis which matches the system axis 4.

As can be seen in the illustration, the intervention needle 11, through which the center beam 12.M of the scanning beam cone 12 passes in the longitudinal direction, is at the same time located on the rotation plane of the gantry. On the one hand, this results in a relatively large scattered radiation component being produced, which has a negative effect on the image display, while on the other hand the beam which passes through the instrument on the longitudinal axis is also attenuated to a very major extent, so that, because of this attenuation, the detector signal has a very high noise component, thus leading to further artifacts. In addition, the long path length through the metallic instrument also results in a significant spectral change to the beam.

Figure 3:
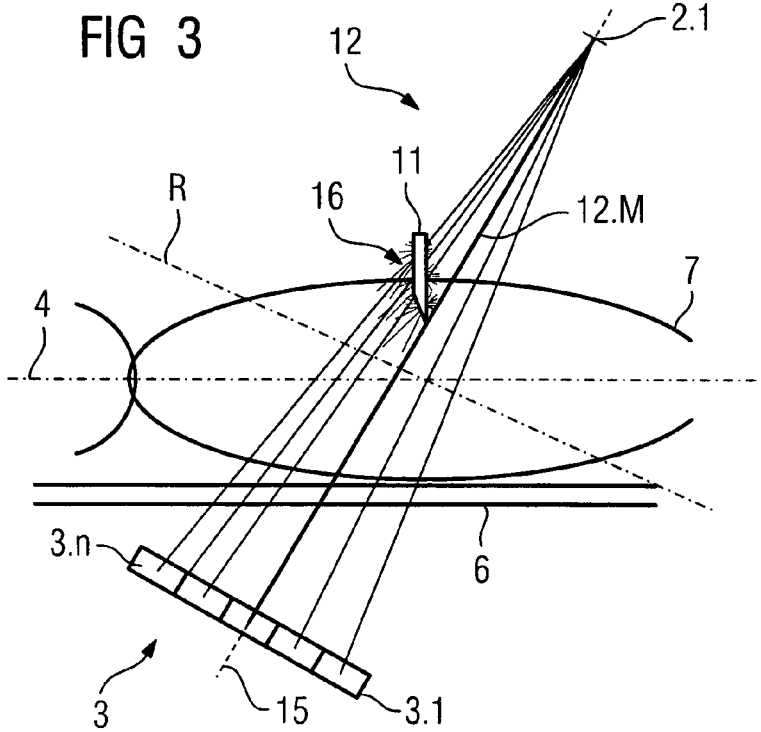
FIG. 3 shows an illustration corresponding to FIG. 2, but with the gantry adjusted according to an embodiment of the invention.

FIG. 3 shows the variant according to an embodiment of the invention of the oblique irradiation of the scanning beam cone. In this case, the rotation plane 15 of the gantry is tilted through an angle $\alpha$ with respect to the system axis 4, so that the X-ray beams in the beam cone 12 pass through the instrument 11 at a steeper angle, thus on the one hand being attenuated less while on the other hand less scattered radiation is emitted which can be measured by the detector elements. Thus, in practice, the intervention needle is undercut in the area of interest on the display, so that this area can be displayed with higher quality.

Figure 4:
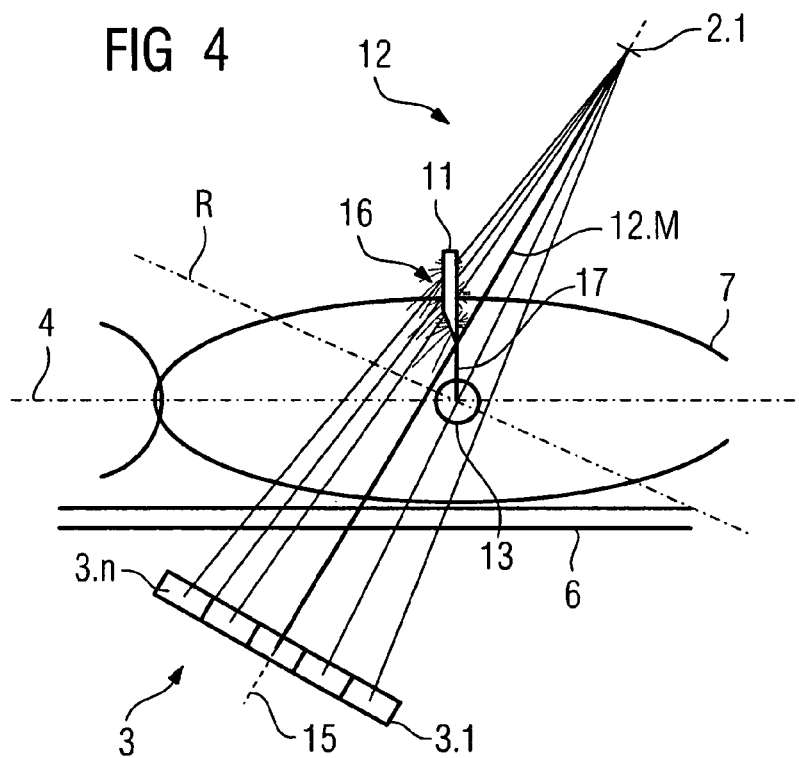
FIG. 4 shows an illustration corresponding to FIG. 3, but with the target region additionally displayed.

FIG. 4 shows a similar illustration to that in FIG. 3, but in this case with the target region 13 for the intervention being marked, thus allowing the gantry to be oriented on the connecting line 17 between the tip of the intervention needle 11 and the target region 13.

Figure 5:
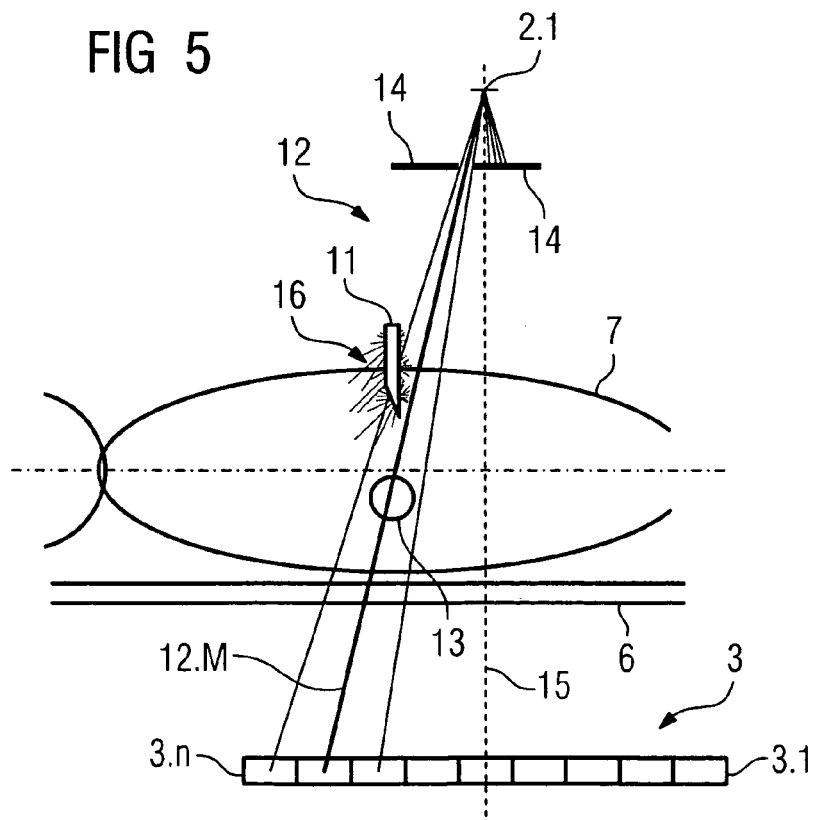
FIG. 5 shows an illustration corresponding to FIG. 4, but without any gantry inclination and with an asymmetrically set beam shutter.

FIG. 5 shows another variant of the alignment of the beam cone 12 with the aid of asymmetric movement of the shutters 14. This is dependent on a relatively broad detector 3 with a large number of detector rows, which allow a beam cone which runs relatively obliquely in the edge area. Because of the asymmetric movement of the shutters 14, only those beams which are arranged at the edge are in this case used for scanning the intervention region, but these are at a sufficiently inclined angle $\alpha$ with respect to the system axis 4. In this case, there is no need to incline the rotation plane 15 of the gantry, so that this involves considerably less mechanical complexity for the production of the CT.

Figure 6:
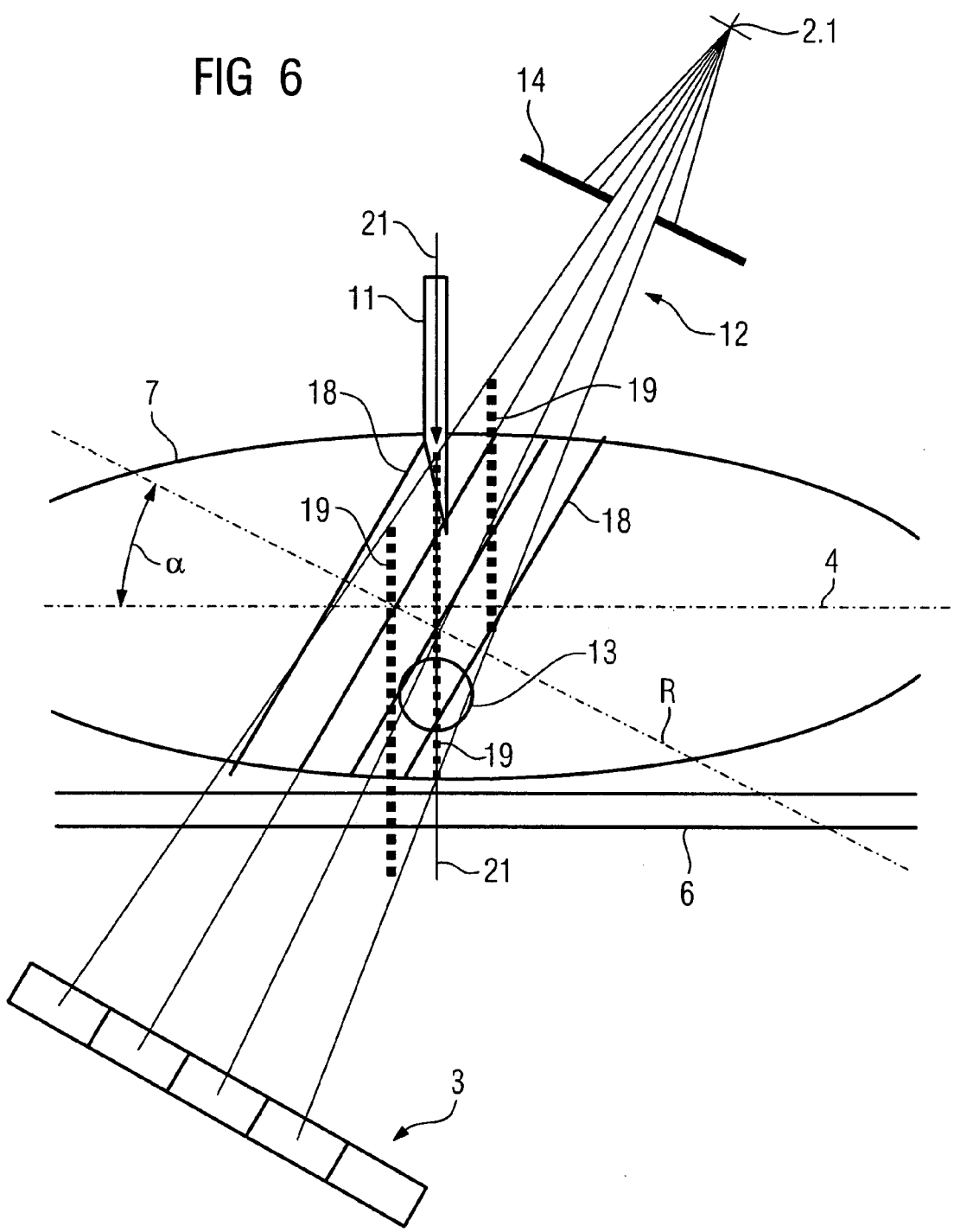
FIG. 6 shows an enlarged illustration of the intervention region with reconstruction planes and additional display planes parallel to the intervention axis.

FIG. 6 once again shows an enlarged illustration of the intervention region with an inclined beam cone 12 with respect to the system axis 4. The beam directions of the beam cone 12 essentially govern the direction of the reconstruction planes 18, although it should be noted the reconstruction is in general not necessarily produced exactly in the same direction as the individual beam, depending on the respective reconstruction method being used, but a certain amount of widening of the beam cone can be ignored and it is assumed that beams which are oriented parallel will pass through the patient.

In this case, however, it should be noted that the present method according to at least one embodiment of the invention is independent of the specific variants of the reconstruction. These discrepancies between the reconstruction planes 18 and the actual beam directions are illustrated considerably exaggerated in the drawing. In addition, three display planes 19 are shown, whose directions are oriented parallel to the intervention axis 21, which in this case passes precisely through the center of the target region 13, starting from the instrument 11. Furthermore, the longitudinal axis 21 of the instrument 11 is shown, for illustrative purposes.

It is thus evident that appropriate beam guidance can in this case result in a reduction in the scattered radiation and the artifacts caused by the instrument 11, with the X-ray radiation passing through the patient in the intervention region without being attenuated by the instrument, and, with appropriate reformatting, the operator nevertheless being provided with a display which is oriented on the longitudinal axis of the instrument, that is to say the intervention axis 21, so that it is still possible to use the normal axial display for the operator.

It is self-evident that the features of embodiment of the invention that have been mentioned above can be used not only in the respectively stated combination but also in other combinations or on their own without departing from the scope of the invention.

In addition, it should also be noted that the method relates to all CT systems, and in particular also to C-arc appliances. C-arc systems, in particular, are particularly suitable for interventions with CT assistance, because of their easy accessibility to the patient.

Thus, overall, at least one embodiment of the invention proposes a method for production of computer-tomographic scans by means of a CT system of a patient during an intervention with an instrument, with an X-ray tube being moved on a rotation plane around the patient in order to produce a beam cone, and a detector with a large number of detector elements measuring the radiation intensity after passing through the patient, and computer-tomographic scans being reconstructed from the measured values in a computation unit with the aid of computer programs. According to the invention, the central direction of the beams of the scanning beam cone is in this case set at an angle to the intervention axis, and at least one slice plane which differs from the rotation plane of the beam cone is displayed on a display.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for production of computer-tomographic scans via a CT system of a patient during an intervention with an instrument, the method comprising:
    moving at least one X-ray tube on a rotation plane around the patient to produce a beam cone, a central direction of beams of the beam cone being set at an angle to an intervention axis and a detector with a plurality of detector elements measuring the radiation intensity after passing through the patient;
    controlling position and orientation of the patient relative to a gantry, which holds the X-ray tube and the detector;
    reconstructing computer-tomographic scans from the measured values; and
    displaying at least one slice plane, which is parallel to the intervention axis, differing from the rotation plane of the beam cone, of a reconstructed computer-tomographic scan on a display, wherein
    an inclination of the angle of the central direction of the scanning beam cone to the intervention axis is produced by inclining the rotation plane of the gantry with respect to a system axis that is substantially parallel to the patient,
    the intervention axis is detected, and
    the maximum angle settable between the central direction of the scanning beam cone and the intervention axis, usable to display a predetermined region on the plane of the intervention axis, is calculated automatically during the scan, and this angle is adjusted such that it is continuously matched.

2. The method as claimed in claim 1, wherein the inclination of the central direction of the scanning beam cone is produced by asymmetric setting of shutters in the beam path.

3. The method as claimed in claim 2, wherein at least one of the slice planes is illustrated at right angles to the system axis.

4. The method as claimed in claim 1, wherein at least one of the slice planes is illustrated at right angles to the system axis.

5. The method as claimed in claim 1, wherein an instrument longitudinal axis is used as the intervention axis, and is detected by evaluation of CT scans.

6. The method as claimed in claim 5, wherein the instrument longitudinal axis takes place by evaluation of the CT scans via a pattern recognition method, which detects the instrument and determines its orientation.

7. The method as claimed in claim 5, wherein the instrument longitudinal axis is determined by transmitters and receivers fitted to the instrument and to the CT system.

8. The method as claimed in claim 1, wherein an instrument longitudinal axis is determined by optical sensors and markings on the instrument.

9. The method as claimed in claim 1, wherein a target region for the intervention is predetermined, and the connection from one part of the instrument to the target region is regarded as the intervention axis.

10. The method as claimed in claim 1, wherein the area between the target region of the intervention and the instrument is used as the predetermined region to be displayed.

11. The method as claimed in claim 1, wherein a predetermined part of the instrument and a predetermined distance in the intervention direction are used as the predetermined region to be displayed.

12. The method as claimed in claim 1, wherein a 2D reconstruction is carried out on the beam plane, but the slices are displayed by reformatting on the plane of the intervention axis.

13. The method as claimed in claim 12, wherein not only axial slice images, but also slice images on the plane of the reconstruction, are displayed.

14. The method as claimed in claim 1, wherein a 3D reconstruction is carried out of a large number of individual voxels.

15. The method as claimed in claim 14, wherein only the voxels of at least one of a predetermined area and an area to be displayed are reconstructed.

16. The method as claimed in claim 15, wherein plane elements which are located in the immediate vicinity of the instrument—and whose orientation is parallel to the intervention direction are selected as the predetermined area of the voxels to be reconstructed.

17. The method as claimed in claim 15, wherein plane elements which are located between the target region and the instrument and whose orientation is parallel to the intervention direction are selected as the predetermined area of the voxels to be reconstructed.

18. The method as claimed in claim 14, wherein both a plane along the intervention axis and an axial display are shown on a display.

19. A computer-tomographic system, comprising:
    an X-ray tube to produce of a beam cone, movable on a rotation plane around the patient, and a detector including a plurality of detector elements, to measure radiation intensity after passing through the patient;
    a control unit to control relative position and orientation of the patient with respect to a gantry, holding the X-ray tube and the detector; and
    a computation unit to evaluate the measured values of the detector and to reconstruct computer-tomographic scans with the aid of computer programs which, when run on the computation and control unit, perform, moving the X-ray tube on a rotation plane around the patient to produce a beam cone, a central direction of beams of the beam cone being set at an angle to an intervention axis, the detector measuring the radiation intensity after passing through the patient, controlling position and orientation of the patient relative to the gantry, reconstructing computer-tomographic scans from the measured values, and displaying at least one slice plane, which is parallel to the intervention axis, differing from the rotation plane of the beam cone, of a reconstructed computer-tomographic scan on a display, wherein the control unit is configured to set an inclination of the angle of the central direction of the scanning beam cone to the intervention axis by inclining the rotation plane of the gantry with respect to a system axis that is substantially parallel to the patient and is configured to detect the intervention axis, and the computation unit is configured to calculate during the scan the maximum angle settable between the central direction of the scanning beam cone and the intervention axis, usable to display a predetermined region on the plane of the intervention axis, the maximum angle being adjusted such that it is continuously matched.

20. The means for controlling is configured to set an inclination of the angle of the central direction of the scanning beam cone to the intervention axis by inclining the rotation plane of the gantry with respect to a system axis that is substantially parallel to the patient and is configured to detect the intervention axis, and the means for controlling is configured to calculate during the scan the maximum angle settable between the central direction of the scanning beam cone and the intervention axis, usable to display a predetermined region on the plane of the intervention axis, the maximum angle being adjusted such that it is continuously matched.

* * * * *